(12) United States Patent  (10) Patent No.: US 9,358,244 B2
Jansen  (45) Date of Patent: Jun. 7, 2016

(54) SOLID DOSAGE FORMS OF OLEYL PHOSPHOCHOLINE

(75) Inventors: Frans Herwig Jansen, Oud-Turnhout (BE); Bruno Jansen, legal representative, Beerse (BE)

(73) Assignee: Oblita Therapeutics BVBA, Zoersel (BE)

( * ) Notice: Subject to any disclaimer, the term of this patent is extended or adjusted under 35 U.S.C. 154(b) by 337 days.

(21) Appl. No.: 13/988,601

(22) PCT Filed: Nov. 21, 2011

(86) PCT No.: PCT/EP2011/070592
§ 371 (c)(1),
(2), (4) Date: Dec. 26, 2013

(87) PCT Pub. No.: WO2012/069427
PCT Pub. Date: May 31, 2012

(65) Prior Publication Data
US 2014/0193493 A1    Jul. 10, 2014

(30) Foreign Application Priority Data

Nov. 22, 2010  (WO) ................. PCT/EP2010/067926

(51) Int. Cl.
*A61K 31/685* (2006.01)
*A61K 9/28* (2006.01)
*A61K 9/20* (2006.01)

(52) U.S. Cl.
CPC ............. *A61K 31/685* (2013.01); *A61K 9/2018* (2013.01); *A61K 9/2054* (2013.01); *A61K 9/2095* (2013.01); *A61K 9/2866* (2013.01); *A61K 9/2077* (2013.01)

(58) Field of Classification Search
None
See application file for complete search history.

(56) References Cited

U.S. PATENT DOCUMENTS

| 5,290,769 A * | 3/1994 | Eibl ..................... A61K 9/0014 514/77 |
| 5,980,915 A | 11/1999 | Eibl et al. |
| 2008/0090781 A1 | 4/2008 | Eibl et al. |
| 2010/0144676 A1 | 6/2010 | Eibl |

FOREIGN PATENT DOCUMENTS

| EP | 0534445 A1 | 3/1993 |
| WO | 9937289 A1 | 7/1999 |
| WO | 2006042751 A2 | 4/2006 |
| WO | 2008116641 A2 | 10/2008 |

* cited by examiner

*Primary Examiner* — Bethany Barham
*Assistant Examiner* — Barbara Frazier
(74) *Attorney, Agent, or Firm* — The Webb Law Firm

(57) ABSTRACT

The present invention relates to solid dosage forms of oleyl phosphocholine (C18:1-PC), or OlPC, for oral administration. Further, the present invention relates to methods for the preparation of the present solid dosage forms and the use thereof as a medicament and especially a medicament for treatment of parasitic diseases, such as leishmaniasis, chagas and malaria, and cancer both in humans and animals. Specifically, the present invention relates to a solid dosage form comprising: 6 to 25 weight % of the solid dosage form oleyl phosphocholine; 20 to 35 weight % of the solid dosage form lactose; 35 to 50 weight % of the solid dosage form cellulose; 5 to 20 weight % of the solid dosage form croscarmellose; 1 to 10 weight % of the solid dosage form hydroxypropylmethyl cellulose; and 0.05 to 1 weight % of the solid dosage form of a lubricant.

11 Claims, 4 Drawing Sheets

SOLID DOSAGE FORMS OF OLEYL PHOSPHOCHOLINE

The present invention relates to solid dosage forms of oleyl phosphocholine (C18:1-PC), or OlPC, for oral administration. Further, the present invention relates to methods for the preparation of the present solid dosage forms and the use thereof as a medicament and especially a medicament for the treatment of parasitic diseases, such as leishmaniasis, chagas and malaria, and cancer both in humans and animals.

Miltefosine (MIL) belongs to the chemical group of alkylphosphocholines and is generally used for the treatment of visceral leishmaniasis (VL). Its particular advantages are an oral route of administration and no cross-resistance is observed with any other first- and second-line anti-leishmaniasis therapy.

Although three new drugs or drug formulations including miltefosine (liposomal amphotericin B, miltefosine and paromomycin) are currently available for the treatment of leishmaniasis, they all suffer either from limitations of cost, toxicity or the need for parenteral administration.

An alternative for miltefosine is the alkylphosphocholine oleyl phosphocholine (C18:1-PC), or OlPC, providing, amongst others, a more effective treatment of parasitic diseases such as leishmaniasis and malaria both in humans and animals.

Although the use of oleyl phosphocholine for the treatment of several diseases is suggested, the suggested formulations of oleyl phosphocholine are generally solutions, suspensions or emulsions. Especially for oral administration, there is a need in the art to provide oleyl phosphocholine in solid dosage forms such as in the form of tablets.

Oleyl phosphocholine has a low melting point (56.3° C.), irregular particle size and shape and is very hygroscopic. These characteristics greatly limit the development of solid dosage forms, such as tablets or capsule fillings, due to difficulties in obtaining a homogeneous dry powder mixture allowing, for example, compression molding into tablets or loading of capsules.

With respect to solid dosage forms of oleyl phosphocholine, it is also important to consider the stability of the formulation. For example, a solid dosage form of oleyl phosphocholine is preferably stable for prolonged periods of time, such as at least 1 year, in a temperature range of 0° C. to 40° C. and a relative humidity in the range of 20% to 80%.

Additional factors to consider in the design of solid dosage forms of oleyl phosphocholine are friability solubility and disintegration characteristics.

It is an object of the present invention, amongst other objects, to provide solid dosage forms of oleyl phosphocholine, and especially solid dosage forms of oleyl phosphocholine for oral administration to both humans and animals meeting at least one, if not all, of the above stated considerations.

The above object, amongst other objects, is met by a solid dosage form of oleyl phosphocholine for oral administration as defined in the appended claims.

Specifically, the above object, amongst other objects, is met by a solid dosage form of oleyl phosphocholine for oral administration comprising:
  6 to 25 weight % of the solid dosage form oleyl phosphocholine;
  75 to 94 weight % of the solid dosage form of one or more pharmaceutically acceptable fillers, disintegrants, binders, lubricants and/or diluents;

Unless indicated otherwise, the weight percentages presented herein are weight percentages as compared to the total weight of the final oral dosage form.

Suitable diluents or fillers according to the present invention are preferably selected from the group consisting of calcium carbonate, calcium phosphate (dibasic), calcium phosphate (tribasic), calcium sulphate, cellulose, microcrystalline cellulose, microcrystalline silicified cellulose, powdered cellulose, dextrates, dextrose, fructose, lactitol, lactose monohydrate, magnesium carbonate, maltitol, maltodextrin, maltose, mannitol, sodium chloride, sorbitol, starch, pregelatinized starch, sucrose, compressible sugar, sugar spheres, talc, xylitol and combinations thereof.

Suitable binders according to the present invention are preferably selected from the group consisting of water, acacia mucilage, alginic acid, carbomer, carboxymethylcellulose calcium, carboxymethylcellulose sodium, microcrystalline cellulose, powdered cellulose, ethyl cellulose, gelatine, liquid glucose, guar gum, hydroxyethyl cellulose, hydroxypropyl cellulose, low substituted hydroxypropyl cellulose, hydroxypropylmethyl cellulose, magnesium aluminum silicate, maltodextrin, methylcellulose, polydextrose, polyethylene oxide, povidone, copovidone, sodium alginate, starch paste, pregelatinized starch, sucrose (syrup) and combinations thereof.

Suitable lubricants according to the present invention are preferably selected from the group consisting of calcium stearate, fumaric acid, glyceryl behenate, glyceryl palmitostearate, hydrogenated vegetable oil, magnesium lauryl sulphate, magnesium stearate, polyethylene glycol 4000 or 6000, sodium lauryl sulphate, sodium stearyl fumarate, starch, stearic acid, talc, zinc stearate and combinations thereof.

Suitable disintegrants according to the present invention are preferably selected from the group consisting of starch, microcrystalline cellulose, alginic acid, methyl cellulose, sodium starch glycolate, croscarmellose sodium, crospovidone, calcium silicate and combinations thereof.

The present solid dosage form provides a friability of less than 1 weight %, preferably less than 0.5 weight %, of the solid dosage form as determined in accordance with the European Pharmacopoeia 2.9.7 standard friability test and/or the present solid dosage form provides a disintegration of less than 15 minutes, preferably less than 10 minutes, as determined in accordance with the European Pharmacopoeia 2.9.1 standard disintegration test (dissolution in 900 ml HCl 0.1 N).

According to a preferred embodiment of the present solid dosage forms, the solid dosage forms provide at least 85 weight % oleyl phosphocholine release within 30 minutes as determined in accordance with the European Pharmacopoeia 2.9.3 standard dissolution test.

According to another preferred embodiment of the present invention, the present solid dosage forms comprise:
  6 to 25 weight % of the solid dosage form oleyl phosphocholine;
  20 to 35 weight % of the solid dosage form of a diluents or filler, preferably selected from the group consisting of calcium carbonate, calcium phosphate (dibasic), calcium phosphate (tribasic), calcium sulphate, cellulose, microcrystalline cellulose, microcrystalline silicified cellulose, powdered cellulose, dextrates, dextrose, fructose, lactitol, lactose monohydrate, magnesium carbonate, maltitol, maltodextrin, maltose, mannitol, sodium chloride, sorbitol, starch, pregelatinized starch, sucrose, compressible sugar, sugar spheres, talc, xylitol and combinations thereof.
  36 to 60 weight % of the solid dosage form of a binder, preferably selected from the group consisting of water, acacia mucilage, alginic acid, carbomer, carboxymethylcellulose calcium, carboxymethycellulose sodium, microcrystalline cellulose, powdered cellulose, ethyl cellulose, gelatine, liquid glucose, guar gum, hydroxyethyl cellulose, hydroxypropyl cellulose, low substituted hydroxypropyl cellulose, hydroxypropylmethyl cellulose, magnesium aluminum silicate, maltodextrin, methylcellulose, polydextrose, polyethylene oxide, povidone, copovidone, sodium alginate, starch paste, pregelatinized starch, Sucrose (syrup) and combinations thereof.

5 to 20 weight % of the solid dosage form of a disintegrants, preferably selected from the group consisting of starch, microcrystalline cellulose, alginic acid, methyl cellulose, sodium starch glycolate, croscarmellose sodium, crospovidone, calcium silicate and combinations thereof; and 0.05 to 1 weight % of the solid dosage form of a lubricant, selected from the group consisting of calcium stearate, fumaric acid, glyceryl behenate, glyceryl palmitostearate, hydrogenated vegetable oil, magnesium lauryl sulphate, magnesium stearate, polyethylene glycol 4000 or 6000, sodium lauryl sulphate, sodium stearyl fumarate, starch, stearic acid, talc, zinc stearate and combinations thereof.

According to still another preferred embodiment of the present invention, the present solid dosage forms comprise:
  6 to 25 weight % of the solid dosage form oleyl phosphocholine;
  20 to 35 weight % of the solid dosage form lactose, preferably lactose monohydrate;
  35 to 50 weight % of the solid dosage form cellulose, preferably microcrystalline cellulose;
  5 to 20 weight % of the solid dosage form croscarmellose, preferably croscarmellose sodium;
  1 to 10 weight % of the solid dosage form hydroxypropylmethyl cellulose; and
  0.05 to 1 weight % of the solid dosage form of a lubricant, preferably magnesium stearate.

According to yet another preferred embodiment of the present invention, the present solid dosage forms comprise:
  10 to 15 weight % of the solid dosage form oleyl phosphocholine;
  25 to 30 weight % of the solid dosage form lactose, preferably lactose monohydrate;
  42 to 47 weight % of the solid dosage form cellulose, preferably microcrystalline cellulose;
  10 to 15 weight % of the solid dosage form croscarmellose, preferably croscarmellose sodium;
  1 to 5 weight % of the solid dosage form hydroxypropylmethyl cellulose; and
  0.1 to 0.3 weight % of the solid dosage form of a lubricant, preferably magnesium stearate.

According to a particularly preferred embodiment of the present invention, the solid dosage forms comprise:
  12 to 14, preferably 13, weight % of the solid dosage form oleyl phosphocholine;
  27 to 29, preferably 28, weight % of the solid dosage form lactose, preferably lactose monohydrate;
  43 to 45, preferably 44, weight % of the solid dosage form cellulose, preferably microcrystalline cellulose;
  11 to 13, preferably 12, weight % of the solid dosage form croscarmellose, preferably croscarmellose sodium;
  2 to 4, preferably 3, weight % of the solid dosage form hydroxypropylmethyl cellulose; and
  0.1 to 0.3, preferably 0.2, weight % of the solid dosage form of a lubricant, preferably magnesium stearate.

The present solid dosage forms preferably are in the form of a tablet, more preferably a tablet comprising an inner core comprised of:
  12 to 14, preferably 13, weight % of the solid dosage form oleyl phosphocholine;
  27 to 29, preferably 28, weight % of the solid dosage form lactose, preferably lactose monohydrate;
  43 to 45, preferably 44, weight % of the solid dosage form cellulose, preferably microcrystalline cellulose;
  5 to 7, preferably 6, weight % of the solid dosage form croscarmellose, preferably croscarmellose sodium;
  2 to 4, preferably 3, weight % of the solid dosage form hydroxypropylmethyl cellulose; and
an outer layer comprised of:
  5 to 7, preferably 6, weight % of the solid dosage form croscarmellose, preferably croscarmellose sodium; and
  0.1 to 0.3, preferably 0.2, weight % of the solid dosage form of a lubricant, preferably magnesium stearate.

According to another aspect, the present invention relates to a method for the preparation of the present solid dosage forms, using the weight percentages presented above, comprising the steps of:
  a) adding to a dry mixture comprising one or more pharmaceutically acceptable diluents/fillers, disintegrants and/or binders water comprising 6 to 25 weight % of the solid dosage form oleyl phosphocholine;
  b) drying and sieving the mixture obtained in step (a);
  c) adding one or more disintegrants and/or lubricants to the mixture obtained in step (b);
  d) mixing the mixture obtained in step (c);
  e) preparing an oral dosage form of the mixture of step (d), preferably by compression molding.

The present OlPC solid dosage forms are obtained by means of compression of granules resulting from wet granulation. This process of pre-treatment of solids prior to compression serves several purposes:
  increasing the particle size to improve flowability;
  improving compression characteristics; and
  preventing particle segregation.

A classic wet granulation process, in a first step, involves the preparation of a dry powder mixture containing the active pharmaceutical ingredient (API), one or more fillers/diluents, a binder, and a disintegrant.

The inability to produce a homogeneous dry mixture with OlPC led to the development of the present alternative wet granulation process. In this novel process, a dry powder mixture is prepared without the presence of the API. The API is dissolved in the granulation liquid and the solution obtained is used to granulate the previously prepared dry powder mixture. This allows a homogeneous distribution of the API in the formulation preventing segregation due to its irregular particle size/shape.

According to a preferred embodiment of this aspect, the present invention relates to a method for the preparation of the present solid dosage forms, using the weight percentages presented above, comprising the steps of:
  a) adding to a dry mixture comprising lactose, preferably lactose monohydrate, cellulose, preferably microcrystalline cellulose, croscarmellose, preferably croscarmellose sodium and hydroxypropylmethyl cellulose water comprising 6 to 25 weight % of the solid dosage form oleyl phosphocholine;
  b) drying and sieving the mixture obtained in step (a);
  c) adding croscarmellose, preferably croscarmellose sodium and a lubricant, preferably magnesium stearate, to the mixture obtained in step (b);
  d) mixing the composition obtained in step (c); and e) preparing an oral dosage form of the mixture of step (d), preferably by compression molding.

The methods according to the present invention preferably comprise a first sieving step, preferably through a 1400 mm sieve, before drying and a second sieving step after drying, preferably through a 710 nm sieve.

According to yet another aspect, the present invention relates to solid dosage forms obtainable by the present methods.

The present invention will be further detailed in the examples below showing non limiting preferred embodiments of the present invention. In the examples presented below, reference is made to figures wherein.

EXAMPLES

List of pharmaceutically acceptable excipients tested in the formulation processes
1) Microcrystalline cellulose (Avicel® PH 101) was used as binder/diluents. Avicel PH 101 has an average particle size of 50 μm and is mostly used for wet-granulation.
2) Lactose monohydrate (Pharmatose®200M) was used as binder/filler. The compound generally improves the tabletting properties of the powder mixture and granules.
3) Polyvinylpyrrolidone (Kollidon®30) is a soluble polyvinylpyrrolidone, which is obtained by radical polymerization of N-vinylpyrrolidone with a molecular weight My of 31.700-51.400 Da.
4) Hydroxypropylmethylcellulose (Methocel® E15 LV). Hydroxypropylmethylcellulose is used as tablet binder. Concentration between 2-5% w/w may be used in either wet- or dry granulation.
5) Croscarmellose sodium (Ac-di-sol®) is used as disintegrant. In the production of tablets, croscarmellose sodium may be used in both direct compression and wet granulation processes. When used in direct granulation, the croscarmellose sodium could be added in both the wet and dry stages of the process (intra and extra granular) so that the full wicking/swelling ability of the disintegrant can be used.
6) Purified water. Purified water can be prepared by distillation, by ion exchange, by reverse osmosis or by any other suitable method from water that complies with the regulations on water intended for human consumption.

Techniques Used to Assess the Suitability of the Present Formulations
1) Disintegration, Ph. Eur. 2.9.1. This test determines whether tablets or capsules disintegrate within the prescribed time when placed in a liquid medium under the experimental conditions. For the purposes of this test, disintegration does not imply complete dissolution of the unit or even of its active constituent. Complete disintegration is defined as that state in which any residue of the unit, except fragments of insoluble coating or capsule shell, remaining on the screen of the test apparatus or adhering to the lower surface of the discs, if used, is a soft mass having no palpably firm core.
2) Flowability, Ph. Eur. 2.9.16. This test determines ability of divided solids (for example, powders and granules) to flow vertically under defined conditions.
3) Friability, Ph. Eur. 2.9.7. This test is designed to evaluate the ability of the tablet to withstand abrasion in packaging, handling and shipping
4) Hardness—Tablet Hardness testing is also called tablet breaking force and measures tablet mechanical integrity.
5) Bulk density, Ph. Eur. 2.9.34. The bulk density of a powder is the ratio of the mass of an untapped powder sample to its volume, including the contribution of the interparticulate void volume. Hence, the bulk density depends on both the density of powder particles and the spatial arrangement of particles in the powder bed. The bulking properties of a powder are dependent upon the preparation, treatment and storage of the sample, i.e. how it has been handled.
6) Dissolution test, Ph. Eur. 2.9.3. Tablets taken orally remain one of the most effective means of treatment available. The effectiveness of such dosage forms relies on the drug dissolving in the fluids of the gastrointestinal tract prior to absorption into the systemic circulation. The rate of dissolution of the tablet or capsule is therefore crucial.

Melting Point Determination and Thermogravimetric Study

The thermal behavior of OlPC was evaluated using a 2920 Modulated DSC (TA Instruments, Leatherhead, UK) equipped with a refrigerated cooling system (RCS). Dry helium at a flow rate of 40 mL/min was used as the purge gas through the DSC cell and 150 Ml/min of nitrogen through the RCS unit.

Samples (±6 mg) were run in closed aluminium pans supplied by TA Instruments; the mass of each empty sample pan was matched with the mass of the empty reference pan to ±0.10 mg. The experimental method consisted of an initial 5 min isothermal equilibration period at 0° C. During the subsequent heating run the following experimental parameters were used: an underlying heating rate of 2° C./min from 0 to 350° C., modulation amplitude of 0.212° C. and a period of 40 s.

Temperature and enthalpic calibration was performed with an indium standard, whereas calibration of the heat capacity was performed with a sapphire standard. The results were analyzed using the TA Instruments Universal Analysis Software.

It was determined that OlPC has a melting point of 56.3° C. Further trials were performed to evaluate the degradation temperature using thermogravimetric analysis (TGA).

Thermogravimetric Analysis (TGA) measures weight changes in a material as a function of temperature (or time) under a controlled atmosphere. Its principal use includes measurement of a material's thermal stability and composition. The TGA analysis was performed using a HR TGA 2950 (TA Instruments, Leatherhead, UK). Samples (±15 mg) were equilibrated at 50° C. and then heated to 500° C. at a heating rate of 10° C./min and the percentage of weight loss was recorded. The OlPC compound show thermal degradation at 159.27° C. with 1% of mass loss.

Spectroscopic Fingerprinting of OlPC

NIR and Raman spectroscopic techniques allow a detailed finger printing of a compound molecular structure and possible changes upon processing.

Raman spectroscopy is a light-scattering process in which the substance under examination is irradiated with intense monochromatic light (usually laser light) and the light scattered from the specimen is analyzed for frequency shift.

Raman spectroscopy is a complementary technique to infrared spectroscopy since the two techniques prone the molecular vibrations in a material, nevertheless both have different relative sensitivity for different functional groups.

A RamanRxn1 spectrometer (Kaiser Optical Systems, Ann Arbor, Mich., USA), equipped with an air-cooled charge coupled device (CCD) detector (back-illuminated deep depletion design) was used in combination with a fiber-optic non-contact probe to collect the powder spectrum. The laser wavelength during the experiments was the 785 nm line from a 785 nm Invictus NIR diode laser. The spectrum was recorded at a resolution of 4 cm$^{-1}$ using a laser power of 400 mW. Data collection, data transfer, and data analysis were automated using the HoloGRAMS data collection software (Kaiser Optical Systems), the HoloREACT reaction analysis and profiling software (Kaiser Optical Systems) and the Matlab software (The Mathworks; version 7.7). A 10 second laser exposure time were used. A Raman spectrum characteristic from OlPC was obtained.

A diffuse reflectance NIR spectrum was collected using a Fourier-Transform NIR spectrometer (Thermo Fisher Scientific, Nicolet Antaris II near-IR analyzer) equipped with an InGaAS detector, a quartz halogen lamp and a fiber optic non-contact probe. Data analysis was done using Thermo Fisher Scientifics' Result software. The spectrum was collected in the 10000-4000 cm$^{-1}$ region with a resolution of 16 cm$^{-1}$ and averaged over 32 scans. A NIR spectrum characteristic from OlPC was obtained.

OlPC Hygroscopicity

Active pharmaceutical ingredients (API) frequently show a propensity to interact with water molecules, leading to absorption of moisture in their bulk structure or adsorption on their surfaces. Such behaviour can critically affect many pharmaceutical properties such as purity, solubility and chemical stability, density, surface area, powder flow, compact ability and crystal form. Compounds may be classified as non-hygroscopic, slightly hygroscopic, moderately hygroscopic, or very hygroscopic, based on the percentage of weight gain during exposure to define humidity conditions at a specific temperature. Dynamic vapor sorption (DVS) analyzes determine hygroscopicity profiles using a very small sample (≈15 mg), and provide both qualitative and quantitative information on water uptake.

Water sorption/desorption isotherm of OlPC was determined gravimetrically at 25° C. (SD, 0.1° C.) using a DVS Advantage 1 with a Cahn D200 microbalance (Surface Measurement Systems, London, UK). Between 10 and 20 mg was weighed in the sample cup of the instrument, subjected to a drying step in order to bring the sample to a constant weight and subsequently exposed to increasing relative humidity (RH) (using 10% increments up to 90%). Following the sorption phase, the sample was exposed to a decreasing RH (in steps of 10% until 0% RH). Each step continued until equilibrium was reached (i.e. when the change in mass smaller than 0.002% per minute during at least 10 min) or until 6 h had passed. The mass change was recorded every minute with a resolution of ±0.1 µg.

The water sorption and desorption profiles of OlPC show that OlPC is a very hygroscopic compound, absorbing 41.67% of water when exposed to 90% RH.

Flow Properties and Corresponding Angle of Repose

Flow properties and corresponding angle of response were determined as described Carr RL. Evaluating flow properties of solids. Chem. Eng 1965; 72: 163-168 using the following criteria:

| Flow properties | Angle of repose (degrees) |
|---|---|
| Excellent | 25-30 |
| Good | 31-35 |
| Fair(aid not needed) | 36-40 |
| Passable (may hang up) | 41-45 |
| Poor (must agitate, vibrate) | 46-55 |
| Very poor | 56-65 |
| Very, very poor | >66 |

HPLC Method for OlPC Quantification in Tablets/Mixture

Equipment Conditions:

Detector type: UV

Wavelength: 206 nm

Column: Lichrosphere® 100rp-8 endcapped (5 µm), Merck, cat. no. 1.50827.0001

Guard column—Lichrosphere® Guard Column RP-8 endcapped, Merck, cat. no. 1.50961.0001

Column temperature: 25° C.

Flow rate: 0.75 mL/min

Injection volume: 30 µL

Mobile phase: Methanol (87.5%)/0.01N HCl (12.5%)

OlPC approximate elution time: 5.30 min

Sample Preparation:

Disperse the amount correspondent to 1 tablet (385.15 mg) in 50 mL of HPLC grade methanol (in case of the tablet it needs to be previously pulverized in a mortar). Sonicate the obtained suspension for 15 min. Stir for 5 min. Afterwards centrifuge at 4000 rpm for 10 minutes. Carefully remove the upper transparent phase and place in a vial for injection.

HPLC Method for OlPC Quantification in 0.1 N HCl

Equipment Conditions:

Detector type: PDA and MS detector

DAD Wavelength: 196 nm

Column: Supleco Discovery HPLC column C8 150*4.6 mm*5 µm

Column temperature: 15° C.

Flow rate: isocratic 1.5 mL/min

Injection volume: 50 µL

Mobile phase: 800 mL acetonitrile. 200 mL water (Mili Q Grade), 500 µL Formic Acid, 100 µL Triethylamine.

Sample preparation: The samples are homogenized, filled into vials and injected.

Formulation of Solid Dosage Forms

Figure 1:
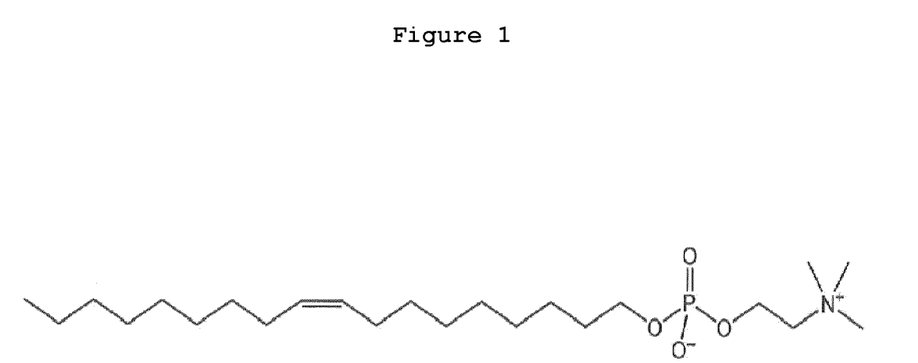
FIG. 1: shows the structural formula of OlPC ($C_{23}H_{48}NO_4P$)
Figure 2:
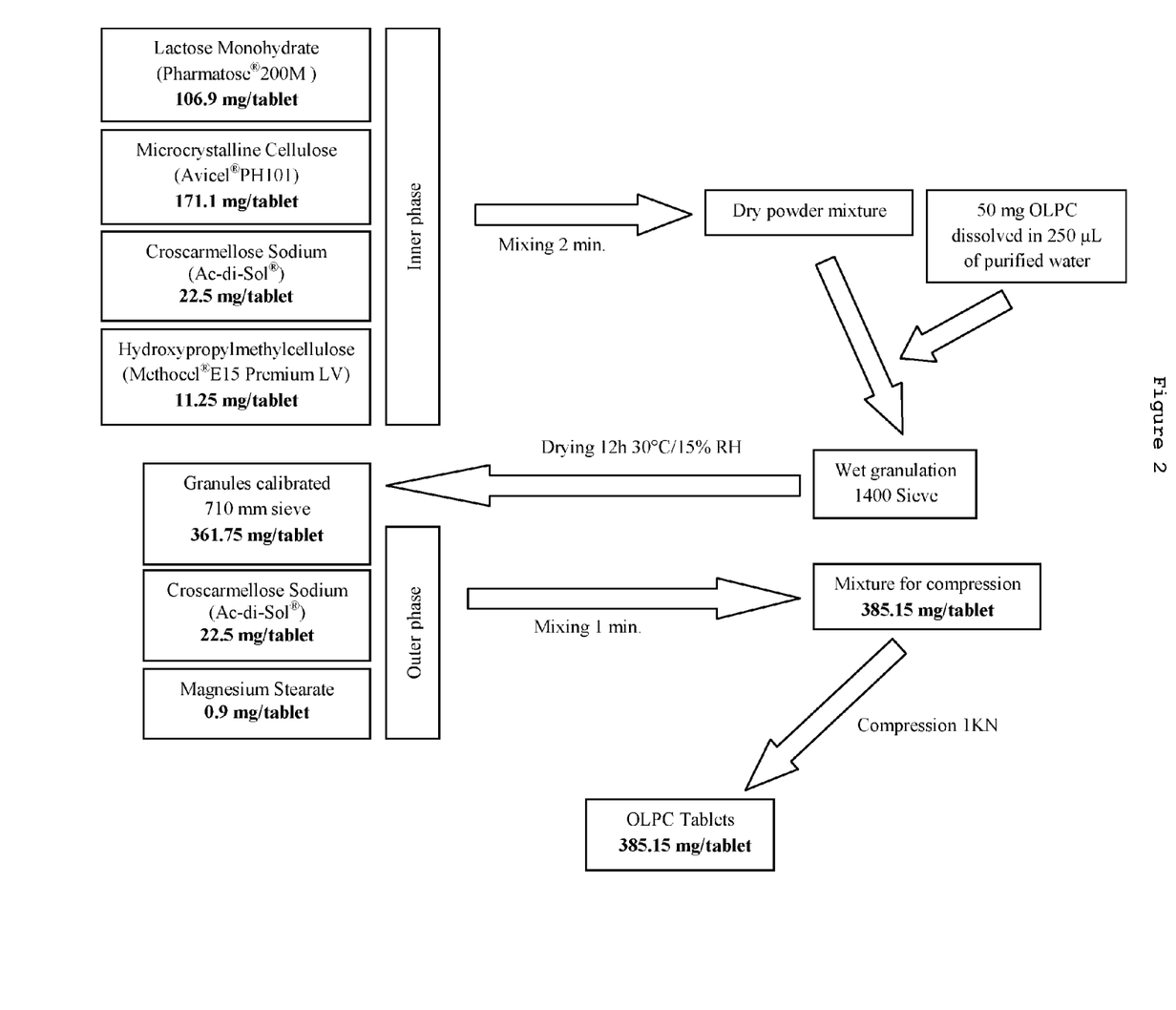
FIG. 2: shows a schematic representation of a preferred formulation process of the present solid dosages forms of oleyl phosphocholine.

FIG. 2 shows a schematic representation of the formulation process used to provide the oleyl phosphocholine solid dosage forms exemplified below.

Example 1

The wet granulation process for OlPC solid dosage formulation requires that OlPC is solubilised in water. OlPC as a water solubility of 0.2 g/ml, which implies that for each tablet with 50 mg of OlPC at least 250 µl of water per tablet has to be incorporated in the dry powder mixture.

A wet granulation mixture was developed (Table 1). The referred dry mixture allows the incorporation (per tablet weight of 315 mg) of 250 µl of OlPC solution for a final dosage of 50 mg. The obtained wet mass was easily passed through a sieve of 1400 mm. After the 12 hours drying period good quality granules were obtained.

TABLE 1

Description of basic, OlPC-free, wet granulation mixture.

| Formulation 01 | Quantitative mg/tablet | Function | Process and conditions |
|---|---|---|---|
| Lactose Monohydrate (Pharmatose ® 200M) | 100 | Filler/diluent | Dry mixing 2 min.   Granulation 1400 mm sieve   Drying 12 h 30° C./15% RH |
| Microcrystalline Cellulose (Avicel ® PH101) | 200 | Filler/diluent | |
| Croscarmellose Sodium(Ac-di-Sol ®) | 12 | Super disintegrant | |
| Polyvinylpyrrolidone (Kollidon ® 30) | 3 | Binder | |
| Dry phase weight: 315 mg | | | |
| Demineralized water 250 µL purified water | | | |
| Granule weight: 315 mg | | | |

Example 2

Incorporation of OlPC into the Formulation

Upon the production of good quality placebo granules, OlPC was introduced into the formulation solubilised in the granulation aqueous solution (Table 2).

TABLE 2

Introduction of OlPC in the granulation aqueous solution.

| Formulation 02 | mg/tablet | Function | Process and conditions |
|---|---|---|---|
| Lactose Monohydrate (Pharmatose ® 200M) | 100 | Filler/diluent | Dry mixing 2 min.   Granulation 1400 mm sieve   Drying 12 h 30° C./15% RH |
| Microcrystalline Cellulose (Avicel ® PH101) | 200 | Filler/diluent | |
| Croscarmellose Sodium (Ac-di-Sol ®) | 12 | Super disintegrant | |
| Polyvinylpyrrolidone (Kollidon ® 30) | 3 | Binder | |
| Dry phase weight: 315 mg | | | |
| OlPC aqueous solution (50 mg OlPC/250 µL purified water) | | | |
| Granules weight: 365 mg | | | |

The wet mass obtained was less easy to granulate, nevertheless good granules were obtained. After a drying period, the granules were compressed into tablets with a 10 mm concave punch and using 1KN compression force. Upon compression, tablets of 365 mg were obtained. Tablet friability and disintegration time were evaluated.

The tablets produced presented high levels of friability and high disintegration time. It was observed that the presence of polyvynilpyrrolidone in solution with OlPC induces the formation of an unknown precipitated which indicates the presence of an incompatibility between the two compounds.

Another binder, hydroxypropylmethylcellulose, was tested and no such incompatibility was observed. Hydroxypropylmethylcellulose was then selected to replace polyvynilpyrrolidone as a binder in the subsequent formulation assays.

Example 3

Replacement of Polyvinylpyrrolidone by Hydroxypropylmethylcellulose

In example 2 the need was demonstrated for the replacement of polyvinylpyrrolidone by hydroxypropylmethylcellulose (HPMC) due to incompatibility of polyvinylpyrrolidone with OlPC in solution. To produce suitable granules with the use of HPMC E15, a higher amount of binder is needed (Table 3).

TABLE 3

Use of hydroxypropylmethycellulose as a binder in the granulation mixture

| Formulation 03 | mg/tablet | Function | Process and conditions | |
|---|---|---|---|---|
| Lactose Monohydrate (Pharmatose ® 200M) | 100 | Filler/diluent | Dry mixing 2 min. Granulation 1400 mm sieve | Drying 12 h 30° C./ 15% RH |
| Microcrystalline Cellulose (Avicel ® PH101) | 200 | Filler/diluent | | |
| Croscarmellose Sodium (Ac-di-Sol ®) | 12 | Super disintegrant | | |
| Hydroxypropylmethycellulose (Methocel ® E15 Premium LV) | 11.25 | Binder | | |
| Dry phase weight: 323.25 mg | | | | |
| OlPC aqueous solution | | | | |
| (50 mg OlPC/250 µL purified water) | | | | |
| Granules weight: 373.25 mg | | | | |

The wet mass produced was easy to granulate and good quality granules were obtained. After 12 hour drying period, the produced granules showed an enhance hardness to the touch, and when placed in water at 37° C., did not to disintegrate before 15 minutes. To obtain good granule disintegration, the amount of Croscarmellose Sodium was selected to be increased.

Example 4

Increasing the Amount of Superdisintegrant Croscarmellose Sodium

The loss of disintegration capability due to the introduction of HPMC was compensated by increasing the amount of Croscarmellose Sodium (Table 4).

TABLE 4

Increasing the amount of the disintegrant croscarmellose Sodium in the granulation mixture.

| Formulation 04 | mg/tablet | Function | Process and conditions |
|---|---|---|---|
| Lactose Monohydrate (Pharmatose ® 200M) | 100 | Filler/diluents | Mixing 2 min. Granulation 1400 mm sieve Drying 12 h 30° C./15% RH |
| Microcrystalline Cellulose (Avicel ® PH101) | 200 | Filler/diluents | |
| Croscarmellose Sodium (Ac-di-Sol ®) | 22.5 | Super disintegrant | |
| Hydroxypropylmethycellulose (Methocel ® E15 Premium LV) | 11.25 | Binder | |
| Dry phase weight: 333.75 mg | | | |
| OlPC aqueous solution | | | |
| (50 mg OlPC/250 µL purified water) | | | |
| Granules weight: 383.75 mg | | | |

The increase of the amount of croscarmellose sodium greatly enhanced the disintegration in water to 2 minutes. Tablets prepared by compression at 1 KN were therefore evaluated regarding disintegration time.

Although the produced granules readily disintegrated in water, upon compression such capability was impaired. To potentiate disintegration capability of the produced tables a similar amount of croscarmellose sodium was then mixed with the dried granules.

Example 5

Incorporation of Croscarmellose Sodium as External Phase

Aiming to improve table disintegration upon compression, an equal amount of croscarmellose sodium was dry mixed with the prepared granules. Due to the particle size difference between croscarmellose sodium and the obtained granules, a step of granule calibration was included to prevent segregation during mixing process. This process includes that the dry granules are force through a sieve of 710 mm and then mixed for 1 minute with croscarmellose sodium (Table 5).

TABLE 5

Incorporation of croscarmellose sodium as external phase to improve disintegration time of the tablets.

| | Formulation 05 | mg/tablet | Function | Process flow and conditions | | | | |
|---|---|---|---|---|---|---|---|---|
| Inner phase | Lactose Monohydrate (Pharmatose ® 200M) | 100 | Filler/diluent | | | | | |
| | Microcrystalline Cellulose (Avicel ® PH101) | 200 | Filler/diluent | | | | | |
| | Croscarmellose Sodium (Ac-di-Sol ®) | 22.5 | Super disintegrant | | | | | |
| | Hydroxypropyl methylcellulose (Methocel ® E15 Premium LV) | 11.25 | Binder | | | | | |
| | Dry mixed phase weight: 333.75 mg | | | Mixing 2 min. | | | | |
| | OlPC aqueous solution (50 mg OlPC/250 µL purified water) | | | | Granulation 1400 mm sieve | Drying 12 h 30° C./15% RH | | |
| | Granules weight: 383.75 mg | | | | | | Calibration 710 mm sieve | |
| Outer phase | Croscarmellose Sodium (Ac-di-Sol ®) | 22.5 | Super disintegrant | | | | | Mixing 1 min. |
| | Dry mixed phase for compression weight: 406.25 mg | | | | | | | Compression 1 kN |

The obtained mixture was compressed at 1 KN to produce tablets of 384.25 mg. The obtained tablets were evaluated regarding disintegration time and friability.

With the introduction of an external phase of croscarmellose sodium, tablet disintegration time was greatly decreased. However, during the compression process it was observed that the tablets had the tendency to stick to the lower punch. Such situation was fixed by the introduction of a lubricant agent such as magnesium stearate on the outer phase of the tablets.

Example 6

Incorporation of a Lubricant Agent (Magnesium Stearate) on the Outer Phase of the Tablets Magnesium stearate was incorporated into the external phase together with croscarmellose sodium to prevent the adhesion of the tablet to the lower punch (Table 6).

TABLE 6

Incorporation of a lubricant agent on the outer phase of the tablets.

| | Formulation 06 | mg/tablet | Function | Process flow and conditions | | | | |
|---|---|---|---|---|---|---|---|---|
| Inner phase | Lactose Monohydrate (Pharmatose ® 200M) | 100 | Filler/diluent | | | | | |
| | Microcrystalline Cellulose (Avicel ® PH101) | 200 | Filler/diluent | | | | | |
| | Croscarmellose Sodium (Ac-di-Sol ®) | 22.5 | Super disintegrant | | | | | |
| | Hydroxypropyl methycellulose (Methocel ® E15 Premium EL) | 11.25 | Binder | | | | | |
| | Dry mixed phase weight: 333.75 mg | | | Mixing 2 min. | | | | |
| | OlPC aqueous solution (50 mg OlPC/250 µL purified water) | | | | Granulation 1400 mm sieve | Drying 12 h 30 C./15% RH | | |
| | Granules weight: 383.75 mg | | | | | | Calibration 710 mm sieve | |
| Outer phase | Croscarmellose Sodium (Ac-di-Sol ®) | 22.5 | Super disintegrant | | | | | Mixing 1 min. |
| | Magnesium Stearate | 0.9 | Lubricant | | | | | |
| | Dry mixed phase for compression weight: 406.25 mg | | | | | | | Compression 1 kN |

The obtained tablets were evaluated regarding disintegration and friability and no effect was observed due to the introduction of the lubricant. No adhesion was observed during compression. However, the obtained tablets still presented high friability.

Example 7

Decreasing of Tablet Friability

Aiming to decrease tablet friability, a change was made in the ratio of the two diluents. Microcrystalline cellulose (MCC) is frequently used with lactose in wet granulation processes. Lactose is known to compact predominantly by brittle fracture while microcrystalline cellulose has a more plastic deformation. This way the ratio of these two fillers is known to affect tablet properties. The wet granulation of mixture with higher ratios of MCC leads to granule densification, loss of compact ability and increased tablet friability. Therefore by reducing the ratio of MCC decrease tablet friability is expected (Table 7).

TABLE 7

Modification of the ratio between Microcrystalline cellulose and Lactose Monohydrate in order to decrease tablet friability.

| | Formulation 07 | mg/tablet | Function | Process flow and conditions | | |
|---|---|---|---|---|---|---|
| Inner phase | Lactose Monohydrate (Pharmatose ® 200M) | 106.9 | Filler/diluents | | | |
| | Microcrystalline Cellulose (Avicel ® PH101) | 171.1 | Filler/diluents | | | |
| | Croscarmellose Sodium (Ac-di-Sol ®) | 22.5 | Super disintegrants | | | |
| | Hydroxypropyl methycellulose (Methocel ® E15 Premium LV) | 11.25 | Binder | | | |
| | Dry mixed phase weight: 311.75 mg | | | Mixing 2 min. | | |
| | OlPC aqueous solution (50 mg OlPC/250 µL purified water) | | | | Granulation 1400 mm sieve | Drying 12 h 30 C./15% RH |
| | Granules weight: 361.75 mg | | | | | Calibration 710 mm sieve |

TABLE 7-continued

Modification of the ratio between Microcrystalline cellulose and Lactose Monohydrate in order to decrease tablet friability.

| | Formulation 07 | mg/tablet | Function | Process flow and conditions |
|---|---|---|---|---|
| Outer phase | Croscarmellose Sodium (Ac-di-Sol ®) | 22.5 | Super disintegrants | Mixing 1 min. |
| | Magnesium Stearate | 0.9 | Lubricant | |
| | Dry mixed phase for compression weight: 385.15 mg | | | Compression 1 kN |

The obtained tablets (weight 385.15 mg) were evaluated and evaluated for friability and disintegration time. They presented satisfactory results (Table 8).

TABLE 8

Evaluation of experimental Formulation 07

| Characteristics Specifications | Tablet | Results |
|---|---|---|
| Dosage | 50 mg Oleylphosphocoline | Not evaluated |
| Drug release | 85% in the first 30 min. | Not evaluated |
| Friability | Less than 1% of the total weight | 0.45% |
| Disintegration | Less than 15 min. | 8 min |

Example 8

Preparation of a 150 Tablet Batch Based on Formulation 7

For further evaluation of mixture and tablet characteristics a batch of 150 tablets was produced based on Formulation 7. The preparation was evaluated for mass-volume relationship (Bulk Density, Tapped Density, Hausner's Ratio, and Compressibility Index) and flow properties (Angle of Repose). The results regarding the OlPC powder/granule mixture for compression are displayed in Table 9.

TABLE 9

Powder mixture for compression rheological evaluation

| Parameter | Results |
|---|---|
| Flowability | Excellent |
| Angle of repose | 29.7° |

Tablet uniformity of mass was performed according to: "Uniformity of mass of single dosage preparations", Ph. Eur. 2.9.5. 20 tablets were weighed and a deviation of 19.26 mg (±5%) was considered. The uniformity of mass test demonstrated little variation among tablets within the batch.

Tablet drug content was determined to evaluate content uniformity of the tablets, The content uniformity test demonstrates that every tablet contains the amount of drug substance intended (50 mg) with little variation among tablets.

Example 9

Preparation of a 1000 Tablet Batch Based on Formulation 7

Based on the data obtained in example 8, a batch 1000 tablets produced for stability testing after packaging in aluminium bags (VaporFlex® VBVF5800-159). The rheological properties of the mixture were determined prior to compression (Table 10).

TABLE 10

Powder mixture for compression rheological evaluation

| Parameter | Results |
|---|---|
| Flowability | Excellent (Annex V) |
| Angle of repose | 29.5° |
| Bulk density | 0.43 g/mL |
| Tapped density | 0.49 g/mL |
| Hausner's ratio | 1.14 |
| Compressibility index | 12% |

Upon the determination of bulk and tapped density the calculated Hausner's ratio, compressibility index and angle of repose are indicators of an excellent flowability.

Tablet drug content was determined to evaluate content uniformity of the tablets. The content uniformity test demonstrates that every tablet contains the amount of drug substance intended (50 mg) with little variation among tablets.

Average uniformity of content in the mixture was performed by means of HPLC. This test is based on the assay of the individual contents of active substance from 3 samples of mixture (each equivalent to the tablet theoretical weight) obtained from 20 tablets pulverized and mixed in a mortar. The average content uniformity in the mixture test confirms the high degree of homogeneity in the distribution of the OlPC within the mixture.

Tablet uniformity of mass was performed according to: "Uniformity of mass of single dosage preparations", Ph. Eur. 2.9.5. 20 tablets were weighed and a deviation of 19.26 mg (±5%) was considered. The uniformity of mass in the OlPC tablets shows a reproducible compression process without significant variations.

Figure 3:
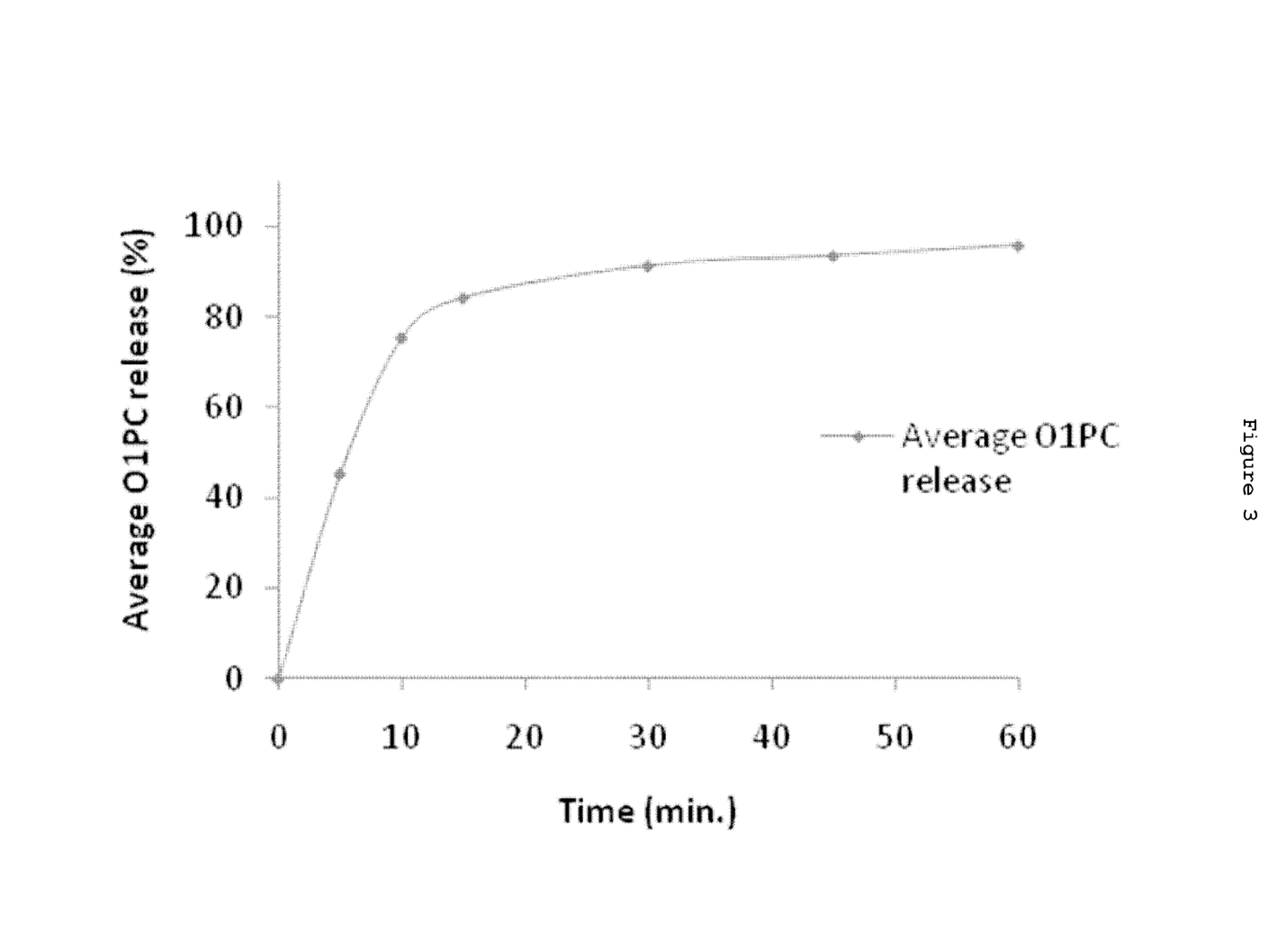
FIG. 3: shows the average dissolution profile of the OlPC tablets.

Drug release from the tablets ("Dissolution test for solid dosage forms", Ph. Eur. 2.9.3) was performed in 900 mL 0.1N HCl, (37.5±0.5° C.), using a paddle apparatus (Ph. Eur. Apparatus 2) at 100 rpm. OlPC aqueous concentration was determined by means of HPLC. Individual and average (FIG. 3) dissolution profiles were determined. The tablets achieve an OlPC release of >85% in less than 30 minutes in compliance with Ph. Eur. 5.17.1.

Example 10

Comparative Curative Efficacy of Miltefosine (MIL) and Oleylphosphocholine (OlPC) Against *Leishmania infantum* in the Hamster Model after Oral Administration at 20 and 40 Mg/Kg for 5 Days Using Different Formulations Miltefosine (MIL) belongs to the chemical group of the alkylphosphocholines and is a marketed drug for the treatment of visceral leishmaniasis (VL). Its particular advantages are oral route of administration and the fact that no cross-resistance exists with any other first-line and second-line anti-*leishmania* therapy.

Although three new drugs or drug formulations (liposomal amphotericin B, miltefosine and paromomycin) are currently available for the treatment of VL, they all suffer either from limitations of cost, toxicity or the need for parenteral administration. Novel alkylphosphocholines and alternative potentially cheaper formulations are being explored as potential added value to the current therapeutic options.

Animals

Golden hamsters (female, 75 g) were allocated randomly to 7 groups with 8 animals per group.
G1: vehicle infected control (VIC): 200 µl blank vehicle orally 5 days
G2: MIL-PBS: 5×40 mg/kg (=98.1 µmol/kg) orally for 5 days
G3: MIL-PBS: 5×20 mg/kg (=49.1 µmol/kg) orally for 5 days
G4: OlPC-PBS: 5×42.5 mg/kg (=98.1 µmol/kg) orally for 5 days
G5: OlPC-PBS: 5×21.2 mg/kg (=49.1 µmol/kg) orally for 5 days
G6: OlPC-liposomes: 5×2.4 ml/kg (=98.1 µmol/kg) orally for 5 days
G7: OlPC-liposomes: 5×1.2 ml/kg (=49.1 µmol/kg) orally for 5 days Drinking water and food were available ad libitum throughout the experiment. The weight of the individual animals did not differ too much from the group mean.

Artificial Infection

*Leishmania infantum* (MHOM/MA (BE)/67) amastigotes were obtained from the spleen of heavily infected donor hamsters. The total parasite burden was determined on Giemsa-stained smears. Amastigotes in the spleen homogenate were concentrated using two centrifugation steps (low speed (300 rpm) with collection of the supernatant–high speed (4200 rpm) with collection of the pellet). The parasite burdens in the spleen were estimated using the Stauber technique and the amastigote suspension was diluted to prepare the infection inocula for intracardial infection containing $2 \times 10^7$ amastigotes/100 µl. At 21 days post infection (=start of treatment), the levels infection were checked in 4 randomly chosen animals by making a smear from a liver biopsy for determination of the parasite burden (cfr. infra).

Test Substances and Formulations

Miltefosine was formulated at 20 mg/ml and 10 mg/ml in PBS and stored at room temperature in the dark. A clear transparent solution was obtained.

OlPC-PBS was formulated at 21.25 mg/ml and 10.63 mg/ml in PBS and stored at room temperature in the dark. A clear transparent solution was obtained.

OlPC-liposome formulation was prepared at 18 mg/ml (dosed at 2.4 ml/kg=120 µl/50 gram). The formulation was diluted 2 times in PBS to obtain a OlPC-formulation of 9 mg/ml (dosed at 1.2 ml/kg=120 µl/50 gram))

Treatment

Oral treatment started 21 days after infection (dpi) and was continued for 5 consecutive days. Dosing volume was 100 µl per 50 gram BW (bodyweight).
Group 1: PBS: 100 µl per 50 gram
Group 2: MIL: 20 mg/ml PBS: 100 µl per 50 gram
Group 3: MIL: 10 mg/ml PBS: 100 µl per 50 gram
Group 4: OlPC-PBS: 21.5 mg/ml PBS: 100 µl per 50 gram
Group 5: OlPC-PBS: 10.6 mg/ml PBS: 100 µl per 50 gram
Group 6: OlPC-liposomes: 18 mg/ml: 120 µl per 50 gram
Group 7: OlPC-liposomes: 9 mg/ml: 120 µl per 50 gram Evaluation Parameters Clinical symptoms: the animals were observed daily for the occurrence/presence of clinical or adverse effects during the 5-week course of the experiment. Body weight: all animals were weighed twice weekly during the course of the experiment to monitor their general health status (severity of infection and toxicity of medication).

Parasite Burden: amastigote burdens in the different target organs (liver, spleen, bone-marrow) were determined 10 days after the last treatment (i.e. day 35 of the experiment). The organs of individual animals were weighed (except bone-marrow); impression smears were fixed in methanol and stained with Giemsa for microscopic evaluation of the number of amastigotes per cell by counting a minimum of 500 nuclei1. The results are expressed as Leishman Donovan Units (LDU)=mean number of amastigotes per nucleus×mg organ weight. Percentage reduction as compared to vehicle-treated infected control animals (VIC) is used as a measure for drug activity. Particularly for spleen and bone-marrow, the viability of possible residual burdens was assessed using the promastigote transformation assay.

Results and Discussion

Treatment was started after verification of the liver parasite burdens 21 days after infection. All four positive controls were adequately infected (1.30±0.3 amastigotes/nucleus in a liver biopsy). All the results are summarized in Table 11:

- The vehicle-treated infected controls (VIC) developed high infection levels in all target organs (liver, spleen and bone marrow)
- The reference drug MIL at 40 mg/kg showed 65% reduction of LDU-values in the liver, 99% in the spleen and 95% in the bone-marrow. At 20 mg/kg, no reduction was obtained in the liver, 61% in the spleen and 39% in the bone marrow.
- OlPC-PBS at 40 mg/kg showed 100% reduction of LDU-values in the liver, spleen and bone-marrow. At 20 mg/kg, 91% reduction was obtained in the liver, 99% in the spleen and 98% in the bone marrow. Minor adverse reactions (closed eyes, agitation) were noted immediately after gavage, disappearing within about half an hour. In the 40 mg/kg group, one hamster died two days after the end of treatment, but is considered not to be drug related.
- OlPC-liposomes at 40 mg/kg showed 100% reduction of LDU-values in the liver, spleen and bone-marrow. At 20 mg/kg, 71% reduction was obtained in the liver, 99% in the spleen and 93% in the bone marrow.
- At necropsy, no gross-pathological lesions were noted in any of the treated animals.

It is concluded that both OlPC formulations are about equipotent, with markedly higher efficacy compared to the reference drug MIL at equivalent dose levels.

TABLE 11

Parasite burdens in *leishmania*-infected hamsters treated orally for 5 days

|  | Liver | | Spleen | | Bone marrow Mean ± SE of amastigotes per nucleus | % red |
|---|---|---|---|---|---|---|
|  | Mean ± SE of LDU | % red | Mean ± SE of LDU | % red | | |
| VIC - PBS | 7981 ± 1366 |  | 479 ± 72 |  | 1.5 ± 0.5 |  |
| Miltefosine 98.1 μmol/kg | 2764 ± 847 | 65 | 3.7 ± 1.67 | 99.2 | 0.1 ± 0.014 | 95 |
| Miltefosine 49.1 μmol/kg | 9017 ± 1489 | 0 | 188 ± 44 | 61 | 1.0 ± 0.34 | 39 |
| OlPC/PBS 98.1 μmol/kg | 29 ± 15 | 99.6 | 0 | 100 | 0 | 100 |
| OlPC/PBS 49.1 μmol/kg | 717 ± 295 | 91 | 3.0 ± 1.45 | 99.4 | 0.03 ± 0.014 | 98 |
| OlPC/liposome 98.1 μmol/kg | 0 | 100 | 0 | 100 | 0 | 100 |
| OlPC/liposome 49.1 μmol/kg | 2283 ± 889 | 71 | 6.0 ± 2.4 | 98.7 | 0.1 ± 0.03 | 93 |

In a follow up experiment, the same experimental protocol was used to compare the efficacy of oral oleyl phosphocholine (OlPC) at total doses of 25, 50 and 100 mg/kg when given as single or multiple oral administrations (5×5, 10 and 20 mg/kg, respectively).

The results show that the overall parasite suppression levels were similar when the doses were given as single or multiple administrations, suggesting that the total exposure (AUC) was more important than high plasmatic concentration (Cmax) for parasite killing.

Interestingly, even single administrations as high as 100 mg/kg were well tolerated in the hamsters and no sign of toxicity was observed during the experiment. Once again the two oleylphosphocholine formulations tested (aqueous and liposomes) were equally well-tolerated.

Figure 4:
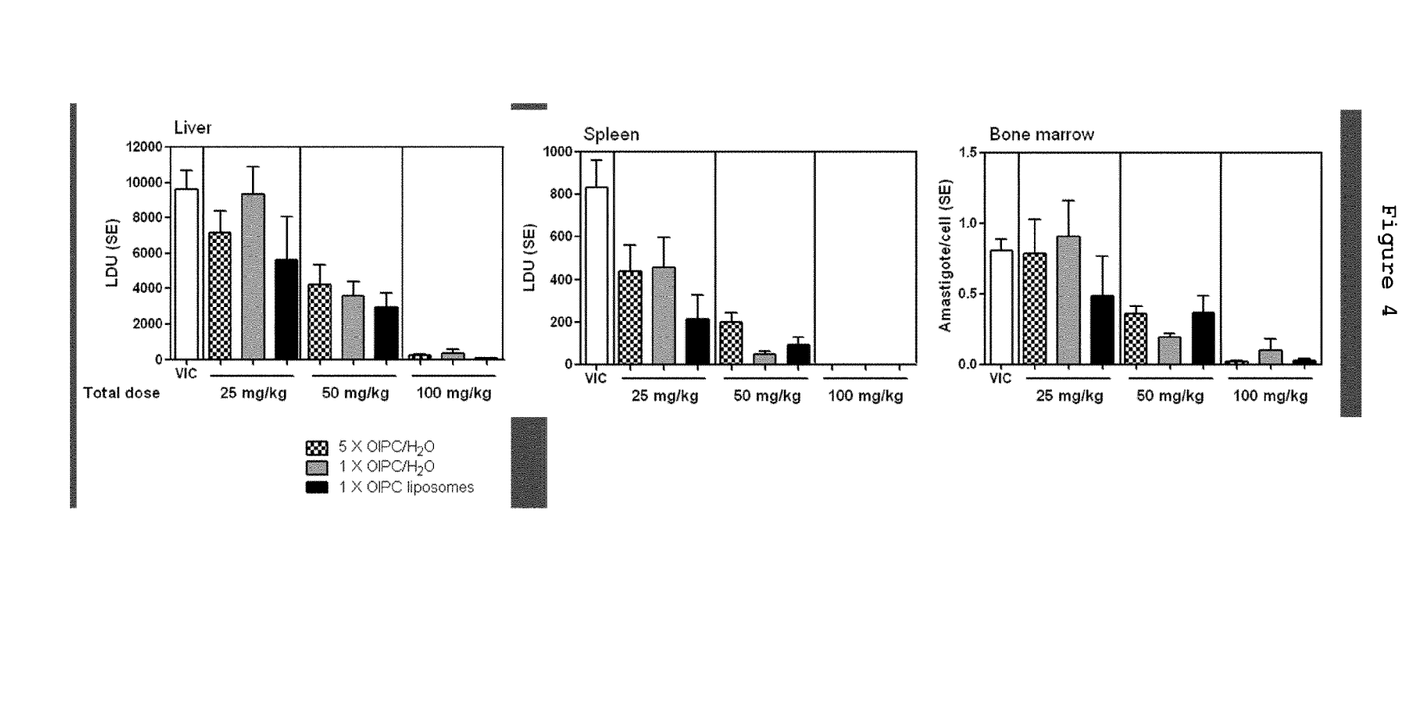
FIG. 4: shows dose-efficacy comparing single and multiple oral administrations of 25, 50, and 100 mg/kg total dose compared to VIC control in A) liver, B) spleen and C) bone marrow.

Female hamsters (n=60) were intracardially infected with $2 \times 10^7$ *Leishmania infantum* (MHOM/MA (BE)/67) amastigotes on day 0. Treatment started at day+21 post infection for 5 consecutive days once daily with a total dose of 25, 50 and 100 m/kg given as single or multiple oral administrations. Amastigote burdens in the different target organs (liver, spleen, bone-marrow) were determined 10 days after the last treatment (day+35). The organs of individual animals were weighed (except bone-marrow); impression smears were fixed in methanol and stained with Giemsa for microscopic evaluation of the number of amastigotes per cell by counting a minimum of 500 nuclei. The results (FIG. 4) are expressed as Leishman Donovan Units (LDU)=mean number of amastigotes per nucleus×mg organ weight.

Treatment of Naturally Infected Dogs

The dose of 4 mg/kg/day oleylphosphocholine was used to treat orally during 14 days a cohort of 6 dogs from a shelter naturally infected with *L. infantum* and classified as clinically sick. The dogs were assessed at the clinical (physical examination and clinic-pathological abnormalities) and parasitological levels at the beginning of the treatment (day 0) and on day 15, 30 and 90.

Regarding tolerance, two of the six dogs treated experienced diarrhea during the first week post-treatment, and a third one had diarrhea and 1 episode of vomiting. The other three dogs tolerated the treatment without any side effect. On day 0 the average clinical score (CS) of the dogs was 19 (range 14-31; severe). This CS went down to 12 (range 7-16) at the end of the treatment period (day 15), then to 5 (range 1-10) on day 30 and to 2 on day 90 (range 0-5), translating an excellent clinical improvement after treatment.

Example 11

Stability of the Solid Dosage OlPC Formulation

1. Aim

To monitor the drug content of OlPC tablets over a 12 month period during storage under controlled environmental conditions.

2. Formulation

| | |
|---|---|
| Oleylphosphocholine | 50 mg |
| Lactose monohydrate (Pharmatose 200M) | 106.9 mg |
| Microcrystalline cellulose (Avicel PH101) | 171.1 mg |
| Croscarmellose sodium (Ac-di-Sol) | 45 mg |
| Hydroxypropylmethylcellulose (Methocel E15 LV) | 11.25 mg |
| Magnesium stearate | 0.9 mg |

3. Methods

Tablet Manufacturing

The tablets (Ø10 mm, weight 385.15 mg) were manufactured according to the process described in example 7 A batch of 1000 tablets (batch 01101007) was prepared under for stability testing under controlled environmental conditions. After manufacturing, the tablets were packaged in hermetically sealed Aluminum sachet (Vaporflex VBVF5800-159) and stored at controlled environmental conditions until further analysis.

Quantification of OlPC Content in Tablets

After 0, 1, 3, 6 and 12 months storage under controlled environmental conditions the drug content of individual OlPC tablets (10 tablets per storage condition) was determined using a HPLC method.

A single OlPC tablet was crushed using mortar and pestle, and an accurately weighed amount was transferred in to a 50 ml volumetric flask. About 35 ml of mobile phase (see below for composition) was added. After 15 min sonication in an ultrasound bath and 5 min stirring to dissolve the API, mobile phase was added to obtain a total volume of 50.0 ml. A homogeneous sample of about 5 ml was transferred to a vial.

To remove the insoluble fraction the sample was centrifuged for 10 min at 4000 rpm. Afterwards an aliquot of the clear supernatant was transferred to an HPLC vial. Standard solutions corresponding to 40, 60, 80, 100 and 120% of the theoretical drug content were prepared by dissolving the required amount of OlPC in methanol.

HPLC Settings:
Column: LichroCart 125-4, Licrospher 100 RP-8 endcapped 5 μm
Pre-column: LichroCart 4-4, Licrospher 100 RP-8 endcapped 5 μm
Mobile phase: Methanol/0.01N HCl (875/125, v/v)
Flow rate: 0.75 ml/min
Injection volume: 30 μl
Detection wavelength: 206 nm
OlPC elution time: ±5.3 min 4. Results The stability study monitored the drug content per tablet (average±standard deviation) in function of storage conditions and storage time. The drug content is expressed as a percentage of the theoretical drug content, i.e. 50 mg per tablet. The results are summarized in table 12 below.

TABLE 12

Stability of the OlPC solid dosage forms

| Storage time (months) | Storage conditions | | | |
|---|---|---|---|---|
| | 2-8° C. | 25° C.-60% RH | 30° C.-65% RH | 40° C.-75% RH |
| 0 | 101.2 ± 2.3% | 101.2 ± 2.3% | 101.2 ± 2.3% | 101.2 ± 2.3% |
| 1 | 101.3 ± 1.7% | — | 101.7 ± 1.2% | 103.0 ± 1.7% |
| 3 | — | 104.2 ± 2.9% | 102.7 ± 1.6% | 102.6 ± 2.0% |
| 6 | 100.4 ± 1.8% | 101.3 ± 1.3% | 101.4 ± 1.2% | 99.1 ± 5.6% |
| 12 | 94.9 ± 1.1% | 95.8 ± 1.3% | 97.7 ± 0.7% | — |

5. Conclusion

This example indicates that the drug content remains stable in the OlPC tablet formulation over at least 12 months at all temperature tested.

The reduction in average drug content after 12 months storage is most probable not indicative of drug degradation as no additional peaks were observed in the chromatograms.

The invention claimed is:

1. Solid dosage form comprising:
   6 to 25 weight % of the solid dosage form oleyl phosphocholine;
   20 to 35 weight % of the solid dosage form lactose;
   35 to 50 weight % of the solid dosage form microcrystalline cellulose;
   5 to 20 weight % of the solid dosage form-croscarmellose;
   1 to 10 weight % of the solid dosage form hydroxypropylmethyl cellulose; and
   0.05 to 1 weight % of the solid dosage form of a lubricant.

2. Solid dosage form according to claim 1, wherein said solid dosage form provides at least 85 weight % oleyl phosphocholine release within 30 minutes as determined in accordance with the European Pharmacopoeia 2.9.3 standard dissolution test.

3. Solid dosage form according to claim 1, comprising:
   10 to 15 weight % of the solid dosage form oleyl phosphocholine;
   25 to 30 weight % of the solid dosage form lactose;
   42 to 47 weight % of the solid dosage form microcrystalline cellulose;
   10 to 15 weight % of the solid dosage form croscarmellose;
   1 to 5 weight % of the solid dosage form hydroxypropylmethyl cellulose; and
   0.1 to 0.3 weight % of the solid dosage form of a lubricant.

4. Solid dosage form according to claim 1, comprising:
   12 to 14 weight % of the solid dosage form oleyl phosphocholine;
   27 to 29 weight % of the solid dosage form lactose;
   43 to 45 weight % of the solid dosage form microcrystalline cellulose;
   11 to 13 weight % of the solid dosage form croscarmellose;
   2 to 4 weight % of the solid dosage form hydroxypropylmethyl cellulose; and
   0.1 to 0.3 weight % of the solid dosage form of a lubricant.

5. Solid dosage form according to claim 1, wherein said form is a tablet or capsule.

6. Solid dosage form of claim 5, comprising an inner core comprised of:
   12 to 14 weight % of the solid dosage form oleyl phosphocholine;
   27 to 29 weight % of the solid dosage form lactose;
   43 to 45 weight % of the solid dosage form microcrystalline cellulose;
   5 to 7 weight % of the solid dosage form-croscarmellose;
   2 to 4 weight % of the solid dosage form hydroxypropylmethyl cellulose; and
   an outer layer comprised of:
   5 to 7 weight % of the solid dosage form croscarmellose; and
   0.1 to 0.3 weight % of the solid dosage form of a lubricant.

7. Method for the preparation of a solid dosage form according to claim 1, said method comprising:
   a) adding to a dry mixture comprising lactose, microcrystalline cellulose, croscarmellose, and hydroxypropylmethyl cellulose water comprising 6 to 25 weight % oleyl phosphocholine;
   b) drying and sieving the mixture obtained in step (a);
   c) adding croscarmellose and a lubricant, to the mixture obtained in step (b);
   d) mixing the composition obtained in step (c); and
   e) preparing an oral dosage form of the mixture of step (d).

8. Method according to claim 7, wherein sieving comprises a first sieving step before drying and a second sieving step after drying.

9. Solid dosage form obtained by the method according to claim 7.

10. A method of treating a parasitic disease in humans or animals comprising administering an oral solid dosage form according to claim 1 to a human or animal.

11. The method of claim 10, wherein the parasitic disease is selected from the group consisting of leishmaniasis, chagas and malaria.

\* \* \* \* \*